United States Patent [19]

Hitzman

[11] 4,044,500
[45] Aug. 30, 1977

[54] INTEGRATED FERMENTATION-PHOTOSYNTHESIS BIOMASS PROCESS

[75] Inventor: Donald O. Hitzman, Bartlesville, Okla.

[73] Assignee: Phillips Petroleum Company, Bartlesville, Okla.

[21] Appl. No.: 432,069

[22] Filed: Jan. 9, 1974

[51] Int. Cl.² .............................................. A01G 7/00
[52] U.S. Cl. ........................................ 47/1.4; 210/15; 195/28 R
[58] Field of Search ...................... 47/1.4, 1.2; 210/10, 210/15; 195/96, 28 R

[56] References Cited

U.S. PATENT DOCUMENTS

| | | | |
|---|---|---|---|
| 2,602,047 | 7/1952 | Calvin et al. | 47/1.4 X |
| 2,732,662 | 1/1956 | Myers et al. | 47/1.4 X |
| 2,867,945 | 1/1959 | Gotaas et al. | 47/1.4 |
| 3,195,271 | 7/1965 | Golueke et al. | 47/1.4 |
| 3,403,471 | 10/1968 | Clement et al. | 47/1.4 |
| 3,431,200 | 3/1969 | Davis et al. | 210/10 |
| 3,520,081 | 7/1970 | Oswald et al. | 47/1.4 |
| 3,521,400 | 7/1970 | Ort | 47/1.4 |
| 3,546,812 | 12/1970 | Kubayashi et al. | 47/1.4 |
| 3,633,547 | 1/1972 | Stevens | 47/1.4 X |
| 3,698,881 | 10/1972 | White | 47/1.4 X |
| 3,768,200 | 10/1973 | Klock | 47/1.4 |
| 3,860,487 | 1/1975 | Emanuel | 47/1.2 X |

Primary Examiner—Robert E. Bagwill
Attorney, Agent, or Firm—Neuman, Williams, Anderson & Olson

[57] ABSTRACT

An integrated process in which aerobic fermentation and photosynthesis are combined. In a first step, fermentation is conducted to produce cells which are recovered. The effluent from the fermentation is used for cultivation of algae with the carbon dioxide produced in the fermentation step being circulated to the algae production step.

4 Claims, 1 Drawing Figure

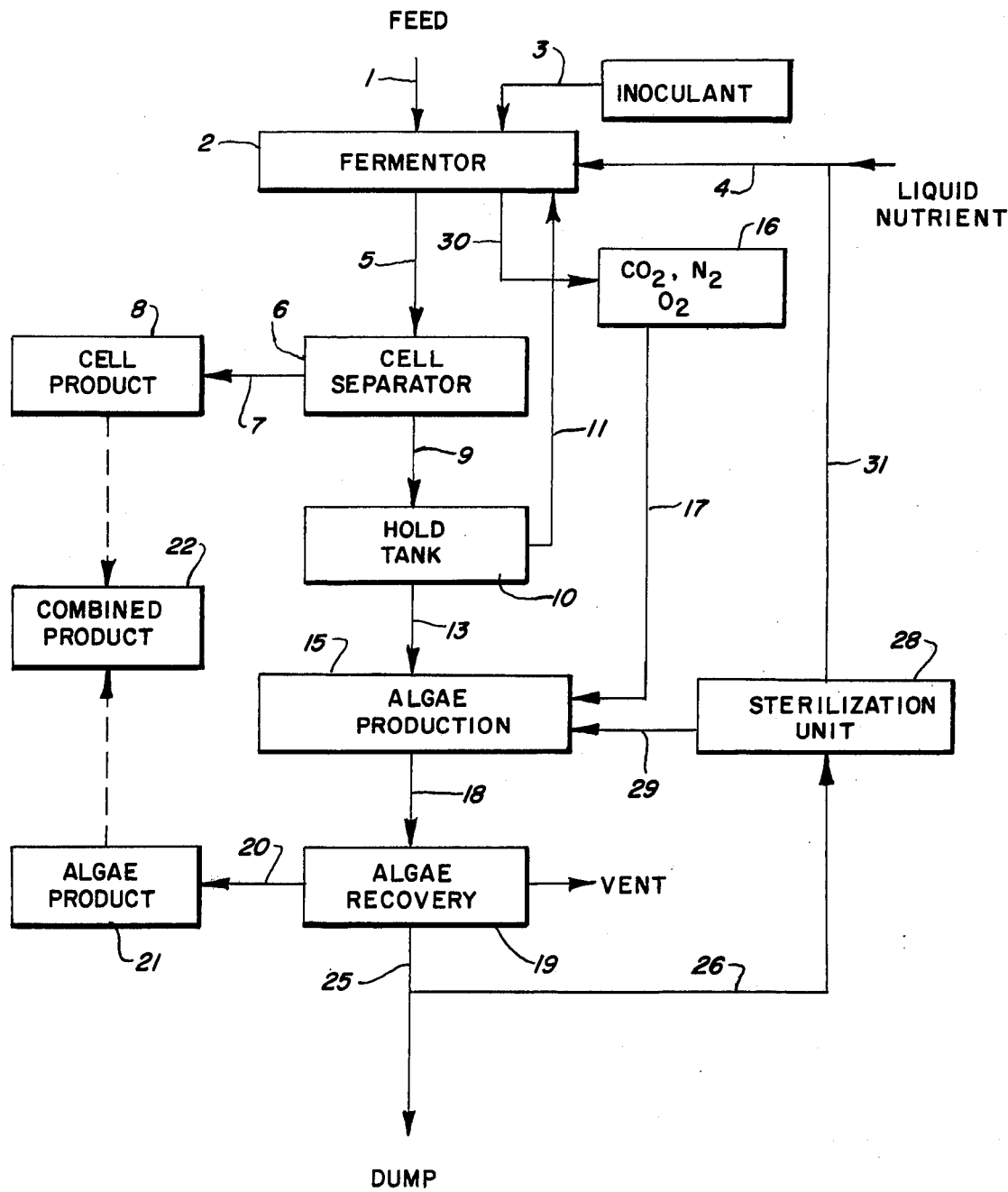

INTEGRATED FERMENTATION-PHOTOSYNTHESIS BIOMASS PROCESS

This invention relates to an integrated process for conducting aerobic fermentations and photosynthesis reactions.

The cultivation of single cell biomasses for human and animal consumption is a growing industry. Two processes, fermentation based on animal metabolism, and photosythesis based on plant metabolism, produce cells which are rich in protein and vitamins so that they are used increasingly to supplement diets, especially diets of domesticated animals. The fermentation process produces single cell proteins from yeasts and bacteria utilizing hydrocarbons or oxygenated carbon compounds as a source of carbon and ammonia or other nitrogeneous compounds as a source of nitrogen. The fermentation process requires oxygen or air and a metabolistic product of the fermentation process is carbon dioxide. The other process, photosynthesis, requires a nitrogen source, carbon dioxide and sunlight or equivalent ultraviolet radiation.

The process of the present invention is an integrated process in which aerobic fermentation and photosynthesis are combined so as to result in a very nearly closed ecology system in which optimum growth conditions are maintained for production of cells in both processes. In the first step, the fermentation is carried out using suitable feedstocks, nutrients and microorganisms for production of cells. The effluent from the fermentation, after cell removal, contains minerals and other materials, some nitrogeneous, which provide an excellent growth medium for photosynthesis reactions in which, for example, algae are produced. The carbon dioxide which is produced in the fermentation step is circulated to the photosynthesis step and provides the required carbon source at higher than normal carbon dioxide partial pressures. The effluent from the photosynthesis, after cell separation, still contains residual minerals and possibly nutrients. This effluent can be sterilized and recycled to the fermentation step as a liquid medium source. Thus, except for the cells, which are harvested in the process, the system is cyclic and produces no effluent which would be considered objectionable.

The integrated process of this invention is illustrated in the schematic process flow diagram of the drawing.

Referring to the drawing, a feedstock for cellular production is introduced from a supply source through line 1 into fermentation vessel or fermentor 2. The feedstock can be any material capable of undergoing aerobic fermentation by means of bacteria, yeasts or other fungi and thus includes hydrocarbon feeds, carbohydrate feeds, alcohols, acids. aldehydes and mixed waste streams from industrial processes. As merely exemplary of the feedstocks there can be mentioned methanol, n-paraffins, molasses, sulfite waste liquids, acetic acid, methane, formaldehyde and the like.

A suitable inoculant, which can be bacteria, yeasts, molds, and the like, is added to fermentor 2 through line 3, while a suitable liquid nutrient medium is introduced through line 4. Again, the particular microorganism employed for the fermentation can be any microorganism capable of promoting aerobic fermentation to produce protein-containing cellular products. Numerous microorganisms of the classes mentioned are known to promote fermentation and the selection of a particular microorganism or a combination thereof can be routinely made by those skilled in the art, depending upon the feedstock to be subjected to fermentation. Illustrative microorganisms include bacteria: Brevibacterium, Nocardia, Corynebacterium, Micrococcus, Arthobacter, Mycobacterium, Streptomyces, Pseudomonas, Bacillus and Actinomyces; yeasts: Candida, Saccharomyces, Torulopsis, Rhodotorula, Hansenula, Brettanomyces, Pichia and Debaryomyces; fungi; Aspergillus, Penicillium, Monillia, Fusarium, Rhizopus, Mucor, Alternia and Fungi imperfectum.

A representative liquid nutrient media is an aqueous solution containing small amounts of certain mineral salts: $NaCl$, $KH_2PO_4$, $K_2HPO_4$, $MgSO_4$, $CaCl_2$, $FeCl_3$. A specific recipe is given below. There are many other base aqueous media which are tailored for best results depending on the organism to be cultured. Such recipes are widely published and one of the most extensive lists of such nutrient media is found in "The American Type Culture Collection" Catalogue of Strains, 10th Edition, 1972, Rockville, Md.

Suitable trace minerals, growth factors, vitamins and the like can also be added to the fermentor 2 in amounts sufficient to provide for the particular needs of the microorganisms utilized. Fermentation is carried out in fermentor 2 under favorable conditions well known to those skilled in the art, depending upon the feedstock and inoculant employed. The present invention is not directed to any particular fermentation but is applicable generally to aerobic fermentations using microorganisms in which protein-containing cellular products are produced. Accordingly, details of specific fermentations or conditions thereof need not be set forth herein since such are well known to those skilled in the art of microbiology.

After fermentation in fermentor 2, the fermented mass is passed through line 5 and subjected to a separation procedure in separator 6 whereby the cellular material is separated from the fermentation broth. Cell separation at 6 comprises such means as coagulation/centrifugation or coagulation/filtration. The cellular products are then passed through line 7 to storage tank 8 wherein they are suitably dried and stored. The biologically active liquid effluent from separator 6 is passed via line 9 to hold tank 10. If desired, the liquid in hold tank 10 can be suitably processed to recover some particular metabolistic product dissolved therein. For example, vitamins, amino acids, antibiotics, organic acids, can be recovered by chemical means, partition chromatography or other methods known in the art.

In any event, a portion which can range from say about 25 to 50% of the volume of the liquid in hold tank 10 is recycled via line 11 to fermentor 2. The remainder of the liquid in hold tank 10 (75 to 50%) is passed via line 13 to algae growth tank 15. The algae growth tank 15 can be any type of sealed culture tank which permits the contents thereof to be irradiated with sunlight or equivalent radiation. The tank 15 is thus covered or sealed with a light transmitting cover which can be a flexible sheet or a rigid panel. Again, the production or cultivation of algae is well known to the art and various known procedures can be employed. Similarly, various algal microorganisms can be used, such as, for example, Chlorella, Spirulina platensis, Spirulina maxima and the like. Generally the pH of the fermentation effluent introduced into algae growth tank 15 is adjusted to a pH of 8.5 to 9.0 and the temperature is maintained at about 30 to 45° C. Carbon dioxide, nitrogen and some oxygen from gas tank 16 is passed via line 17 and sparged into algae growth tank 15. The gas tank 16 receives carbon dioxide, nitrogen and some oxygen from fermentor 2 by way of line 30.

After growth, the algae are transferred via line 18 and subjected to filtration in filter 19. The algae cells can then be passed via line 20 to storage tank 21 where they can be suitably dried. If desired, the dried algae can be sent to storage tank 22 where they can be combined with the cells obtained by fermentation in fermentor 2. Gas can be vented from algae growth tank 15 through gas vent 24. Waste liquid can be removed from algae growth tank 15 through line 25 and removed from the system, or more preferably, it can be passed through line 26 to sterilizer 28, which can be a conventional liquid sterilizer. After sterilization the liquid waste stream can be recycled through line 29 to algae growth tank 15 or through line 31 for admixture with fresh liquid nutrient in line 4.

The following specific example illustrates the integrated process of this invention.

EXAMPLE

A 14-liter New Brunswick stirred fermentor suitably rigged for continuous fermentation and temperature controlled in the range of 32°–40° C. is charged with 7 liters suitable base medium [1] and with 500 cubic centimeters of the inoculum pf Pseudomonas sp. Pseudomonas methanica NRRL-3449*. Materials are charged to the reactor and effluent removed until the bacteria has reached an exponential rate of growth and a steady state has been reached. The following data illustrate steadystate fermentor operation (47–70 hours from start-up).
*Identification assigned by Northern Utilization Research and Development Division, Peoria, Illinois.

| Run 1 | |
|---|---|
| Conditions During Run | |
| Base Medium[1] | BH6[1] |
| Air Input | 10 liters/min |
| Stirrer | 1,000 r.p.m. |
| Growth Factors | none |
| Feed Rates | |
| Methanol Formaldehyde Product[2] | 0.1452 liter/hr |
| NH$_4$OH(22–26% NH$_3$)[3] | 0.0291 liter/hr |
| Base Medium[1] | 1.200 liter/hr |
| Trace Minerals[4] | 1.016 liter/hr |
| Total Feed Rate | 1.3708 liter/hr |
| Steady-State Fermentor Volume | 3.5 l |
| Alcohol Content of Effluent | 1.13% |
| Based on these conditions the following calculations can be made: | |
| Retention Time in Fermentor | 2.55 hr |
| cell Concentration (dry weight) | 26.1 g/liter |
| Yield of Dried Cells/100 lb of Methanol Consumed | 36.15 lb |
| Yield of Dried Cells/100 lb of Methane Consumed[5] | 72.3 lb |
| Percent Protein of Cells[6] | 69.4% |
| Fermentor Productivity[7] | 10.23 g/liter/hr |

[1] BH6 Base Medium has the following amounts of materials per liter of aqueous solution:

| | |
|---|---|
| KH$_2$PO$_4$ | 2.5 g |
| K$_2$HPO$_4$ | 2.5 g |
| (NH$_4$)$_2$SO$_4$ | 2.0 g |
| NaCl | 0.1 g |
| MgSO$_4$ . 7H$_2$O | 3.0 g |
| CaCl$_2$ | 0.04 g |
| Trace Minerals Solution[4] | 10 ml. |

[2] Methanol Formaldehyde Product is Comprised thus:
14 parts Methanol
1 part 37% aqueous formaldehyde
[3] NH$_4$OH was admixed with the Methanol - Formaldehyde Product prior to passing to the fermentor.

[4] Trace Mineral solution has the following amounts of the following compounds per liter of aqueous solution:

| Run 1 | |
|---|---|
| CuSO$_4$ . 5H$_2$O | 0.06 g |
| KI | 0.08 g |
| FeCl$_3$ . 6H$_2$O | 4.80 g |
| MnSO$_4$ . H$_2$O | 0.30 g |
| Na$_2$MoO$_4$ . 2H$_2$O | 0.20 g |
| ZnSO$_4$ . 7H$_2$O | 2.00 g |
| H$_3$BO$_3$ | 0.02 g |

[5] Assuming 100% of theoretical conversion of CH$_4$ to CH$_3$OH if methane is first oxidized to methanol.

[6] Percent protein equals percent nitrogen × 6.25.

[7] Fermentor Productivity is in grams of dried cells per liter of ferment per hour retention time in fermentor.

The liquid effluent from the fermentation reactor is collected after separation of the cells and its pH is adjusted to a value of about 8.5 – 9.0 using sodium carbonate salt or solution. For optimum algae growth the liquid medium should have a temperature between 30° and 45° C. and if required, the temperature is adjusted before introducing the liquid into the algae growth tank 15.

An experimental size algae growth tank is a vessel 3 × 1 × 0.1 meter having a 0.50 m well at one end capped by a fritted stainless steel plate through which carbon dioxide enriched gas is sparged into the tank. It is covered with a 5 mil sheet of polyethylene to keep a positive pressure on the liquid surface.

The feed gas for algae production is the effluent gas stream from the fermentor, augmented when required by additional carbon dioxide so that its carbon dioxide concentration is between 10 and 12 volume percent. The flow of gas is adjusted to about 500 l/hr.

Calculations have been made that illumination of 20–30000 lux is required for optimum algae growth, which can be natural sunlight or artificial light. In the experimental set-up, artifical light is used. The consumption of carbon dioxide is 12 l/m$^2$/day for a production of about 15g/m$^2$/day of dried algae product.

As will be seen from the foregoing, the integrated process of this invention makes possible the economic utilization of the waste effluent from the fermentor. Thus, the two waste streams from the fermentation operation, i.e. the spent medium and the carbon dioxide enriched off-gas, are used advantageously to produce protein. This utilization of normal wastes is both economically and ecologically advantageous.

Those modifications and equivalents which fall within the spirit of the invention are to be considered a part thereof.

What is claimed is:

1. A process which comprises fermenting under aerobic conditions a fermentable feed selected from the group consisting of hydrocarbons, carbohydrates, alcohols, acids, aldehydes and industrial waste streams to produce a protein cellular product, separating the protein cellular product from the spent liquid fermentation effluent, recycling a portion of the spent liquid fermentation effluent to the fermentation and passing the remainder of the spent liquid fermentation effluent to a cultivation tank, inoculating, cultivating and propagating algal microorganisms therein while irradiating same with light, separating the algae from the waste liquid, sterilizing said last-mentioned waste liquid and then recycling the last-mentioned waste liquid to the fermentation.

2. A process in accordance with claim 1 wherein the fermentable feed is selected from methanol, normal paraffins, molasses, sulfite waste liquids, acetic acid, methane and formaldehyde.

3. A process in accordance with claim 1 wherein gases produced in said fermentation are transferred to the cultivation tank wherein inoculation, cultivation and propagation of algae takes place.

4. A process in accordance with claim 1 wherein after separating the protein cellular product from the spent fermentation effluent said cellular product is combined with the algae produced according to claim 1.

* * * * *